United States Patent [19]

Genshaw

[11] Patent Number: 4,772,561
[45] Date of Patent: Sep. 20, 1988

[54] TEST DEVICE AND METHOD OF DETERMINING CONCENTRATION OF A SAMPLE COMPONENT

[75] Inventor: Marvin A. Genshaw, Elkhart, Ind.
[73] Assignee: Miles Inc., Elkhart, Ind.
[21] Appl. No.: 814,746
[22] Filed: Dec. 23, 1985
[51] Int. Cl.$^4$ ............................................. G01N 31/22
[52] U.S. Cl. ..................... 436/169; 422/56; 422/58; 435/14; 435/10; 436/71; 436/95
[58] Field of Search .............................. 422/56, 58, 66; 436/169, 164, 166, 170; 356/306, 417

[56] References Cited

U.S. PATENT DOCUMENTS

| | | | |
|---|---|---|---|
| 3,211,050 | 10/1965 | Pelavin | 356/306 |
| 3,963,442 | 6/1976 | Bullard et al. | 436/165 |
| 4,125,372 | 11/1978 | Kawai et al. | 422/56 |
| 4,160,646 | 7/1979 | Furutani et al. | 436/169 |
| 4,250,257 | 2/1981 | Lee | 422/66 |
| 4,321,465 | 3/1982 | Stover et al. | 250/255 |

FOREIGN PATENT DOCUMENTS

2803109  7/1979  Fed. Rep. of Germany ........ 436/66

Primary Examiner—Michael S. Marcus
Attorney, Agent, or Firm—Roger N. Coe

[57] ABSTRACT

The precision in reflectance or absorption measurements used to determine the presence and concentration of a component in an assay liquid is unexpectedly increased to essentially eliminate the variability of different reactant carriers and variability in reflectance or absorption instruments by including, either within the reactant carrier or within the assay liquid sample, in addition to a primary color forming or color changing indicator, a secondary inert colorant compound or dye having a light absorption wavelength peak separated from a light absorption wavelength peak of the primary indicator or chromogen by at least 80 nm. To achieve the full advantage of the present invention, the colorant material or marker should be inert to the reactant system in the carrier and should be inert to the assay liquid to provide a light reflectance or light absorption response essentially distinct from the light reflectance response of the primary chromogen to compensate for measurement variability. In this manner, any inaccuracy obtained from a reflectance or absorption measurement of the secondary colorant marker, incorporated into the carrier or into the assay sample in known concentration, can be used for compensation of a reflectance or absorption measurement of the primary color formed as a result of interaction or reaction of the test sample with the reagent composition, and, therefore, the concentration measurement of a predetermined component of the assay liquid.

14 Claims, 4 Drawing Sheets

TEST DEVICE AND METHOD OF DETERMINING CONCENTRATION OF A SAMPLE COMPONENT

FIELD OF THE INVENTION

The present invention relates to a new and improved test device for the assay of fluids to determine the presence of a chemical compound, such as glucose; lower alcohols, such as ethanol; cholesterol; uric acid; hemoglobin; and potassium and, particularly to a new and improved method and device of increased accuracy and correction of reflectance readings indicative of a concentration of a chemical compound in the test fluid. More particularly, the present invention relates to a new and improved reagent strip including a reactant system capable of forming a primary chromogen and a secondary, inert chromogen material incorporated into the reactant system in a known concentration, for correction of a reflectance reading measured for the primary chromogen.

BACKGROUND OF THE INVENTION AND PRIOR ART

It is well known to measure concentrations of various compounds by the initial measurement of a known concentration of one or more compounds, such as in gas chromatography, to obtain one or more graphic peak heights or areas used as a standard for the calculation of an unknown concentration of one or more other compounds in a sample. One widely used technique of quantitation using both peak heights and peak areas involves the addition of a known compound having similar properties to the unknown, or analyte, being measured. In accordance with this approach, a known compound at a fixed concentration is added to the unknown sample to give a separate peak in the chromatogram and the separate peak is used as an internal marker to adjust the measured concentration of unknowns proportional to the reading inaccuracy of the marker.

In this manner, it is theorized that any loss or gain in the measurement of the unknown is accompanied by an exactly equal loss or gain in the measurement of the internal marker compound so that a correction factor, defined from an inaccurate detector response for the marker, is applied to the detector response for the unknown. The equality of loss or gain in measurement of the compound of interest and the internal marker, however, depends upon a number of factors, particularly the structural equivalence of the components of interest and the internal marker compound; specifically their equivalence in extraction, solvent solubility, reaction, detector response and capacity for any other process steps applied to the marker and test sample to achieve a measurable signal from the measuring apparatus.

As set forth by Snyder and Kirkland, Introduction to Modern Liquid Chromatopgraphy, Second Edition, page 554, the selection for known marker compounds are very ominous: The internal marker must have a completely resolved peak with no interference; it must elute close to compound(s) of interest (similar k' values); it must behave equivalently to compound(s) of interest for analyses involving pretreatments, derivative formation, etc.; more than one internal marker compound may be required for multicomponent mixtures to achieve highest precision; it must be added at a concentration that will produce a peak-area or peak-height ratio of about unity with the compound(s) of interest; it must not be present in the original sample; it must be stable; and it must be unreactive with test sample components, column packing, or mobile phase.

Because of these ominous requirements and, therefore, the necessity of using less than perfect internal marker components, the addition of known, integral marker compounds as a method of reducing inaccuracies has been confined, for the most part, to gas chromatographic analysis and used very little in infrared and emission spectroscopy, and has not been used in test samples measured for reflectance or absorption for quantitative analyses.

Reagent strips are widely used for the quantitative analysis of low concentrations of various compounds, particularly for analyses of pathologically significant substances in body fluids, such as the quantitative analysis of glucose in blood. Typically, a reagent strip includes a reagent liquid-absorbant or adsorbant material carrying a reagent capable of reaction with the compound of interest in the test sample. Quantitative measurement of the unknown is achieved by detecting the appearance of a reaction product or the disappearance of a known reactant impregnated in a known concentration in the reagent strip. For example, the Ames Division, Miles Laboratories, Inc. manufactures a number of different reagent strips including reagents reactive with glucose; cholesterol; triglycerides; uric acid; blood urea nitrogen (BUN); hemoglobin; potassium and other pathologically significant substances. Generally, the reaction products absorbed in the reagent strip are quantitatively measured on a reflectance photometer. The measured reflectance of the reagent strip, after reaction of the body fluid with the reagent strip absorbed reactant yields a quantitative colorimetric determination of the concentration of the detected compound. These reagent strips are quite effective for quantitative analyses and, generally, are precise within about $\pm 2$ to $10\%$ variation.

It has been found that the most significant reasons for variation in quantitative measurement from reagent strips, other than the normal chemical variability encountered in all clinical reagents, are (1) the variability of the reagent strips, particularly in reflectance and absorption or adsorption capacity; and (2) variability of instruments (detector response) used to measure the amount of reaction product formed, or measure the disappearance of a reactant. In accordance with the present invention, the reagent strips, or other reactant or catalyst-containing material include an inert chromogen marker in a known concentration yielding a colorimetric reflectance response having a wavelength peak separated from a colorimetric response of a chromogen dye colorimetrically responsive to a concentration of a test sample component.

It is known that reflectance or absorption readings measured at significantly different wavelengths vary considerably. Therefore, previous efforts to correct reflectance (or absorption) readings used to determine, quantitatively, an assay liquid component have been directed to the initial calibration of the instrument by obtaining readings at known concentrations of the reagent strip chromogen measured at low and high wavelengths.

In accordance with the present invention, it has been found that the inaccuracy in reflectance or absorption readings obtained from a known inert, secondary colorant material is a direct indication of the inaccuracy in reflectance or absorption measurements of a primary chromogen material formed by interaction of the test liquid with a reagent composition, regardless of measurement wavelength of the chromogen or concentration of the component quantitatively measured in the assay liquid. This feature is most surprising and enables approximate doubling of the accuracy of concentration measurements compared to those obtained without incorporating a secondary, inert colorant material in addition to the primary chromogen.

SUMMARY OF THE INVENTION

Briefly, the present invention is directed to a new and improved reactant carrier or reagent strip and to a method of determining, more precisely, the presence and relative concentration of a component in a test sample. The reactant carrier or reagent strip includes a matrix of a reactant-absorbing or reactant-adsorbing material, such as cellulose, capable of carrying a reactant system selected for interaction with a colorimetric predetermined sample component to produce a detectable response. Suitable reactant-absorbing or reactant-adsorbing materials forming the matrix or carrier of the reagent strip include bibulous materials, such as filter paper; foams; nonwoven fabrics; gel foams; phase inversion films; any other suitable, inert porous matrices; polymer films and the like. As well known in the art, reagent strips usually are formed of filter paper impregnated with one or more reactants and/or reaction catalysts secured to a support layer such as an inert polymeric sheet material. To achieve an interaction or reaction with a predetermined component of a test sample, the reagent strip is either dipped into the sample or the test sample is pipetted onto the reagent strip. Chemical reactions or interactions then produce changes in the reflectance of the reagent strip. Concentration of the predetermined component of the sample then is determined either by visual comparison to a color chart to obtain somewhat crude quantitative values or the reagent strip is disposed in a reflectance instrument to provide more precise quantitative results.

In accordance with the present invention, it has been found that the precision in reflectance or absorption measurements used to determine the presence and concentration of a component in an assay liquid is unexpectedly increased to essentially eliminate the variability of different reactant carriers and variability in reflectance or absorption instruments by including, either within the reactant carrier or within the assay liquid sample, in addition to a primary color forming or color changing indicator, a secondary, inert colorant compound or dye having a light absorption wavelength peak separated from a light absorption wavelength peak of the primary indicator or chromogen by at least 80 nanometers (nm) and preferably at least 120 nm. To achieve the full advantage of the present invention, the colorant material or marker should be inert to the reactant system in the carrier and should be inert to the assay liquid to provide a light reflectance or light absorption response essentially distinct from the light reflectance response of the primary chromogen to compensate for measurement variability. In this manner, any inaccuracy obtained from a reflectance or absorption measurement of the secondary colorant marker, incorporated into the carrier or into the assay sample in known concentration, can be used for compensation of a reflectance or absorption measurement of the primary color formed as a result of interaction or reaction of the test sample with the reagent composition, and, therefore, the concentration measurement of a predetermined component of the assay liquid.

Quite unexpectedly, it has been found that the incorporation of a secondary, inert colorant marker into the reagent or reactant carrier or into the sample liquid, in a known concentration, provides an accuracy correction factor usable to correct the reflectance or absorption measurement obtained from the primary color formation or color change resulting from reaction or interaction of a sample component with a reagent strip reactant.

Accordingly, an object of the present invention is to provide a new and improved method and test device for determining the relative concentration of a chemical compound in a liquid.

Another object of the present ivention is to provide a new and improved method and test device for reaction with glucose, cholesterol, uric acid, hemoglobin or potassium in a test fluid to produce a colorimetrically detectable change in the device in a primary and a secondary, inert chromogen dye for reflectance measurements at two, distinct wavelengths for reflectance measurement correction of the primary chromogen.

Still another object of the present invention is to provide a new and improved method and reagent strip wherein two materials are incorporated into the reagent system, either in the reagent strip or in the test sample, wherein a secondary colored material, in a known concentration provides a reflectance reading correction factor for the measured reflectance of a primary color forming material for accuracy in concentration measurement.

The above and other objects and advantages of the present invention will become apparent from the following detailed description of the present invention taken in conjunction with the drawings.

DETAILED DESCRIPTION OF THE PREFERRED EMBODIMENTS

The article and methods of the present invention are useful in determining the relative ccncentrations of any assay liquid component capable of reaction or interaction with a reactant composition to produce a detectable color change detectable in a light reflectance or absorption instrument. Suitable reagent strips into which the secondary, inert colorant marker can be incorporated include those manufactured by the Ames Division of Miles Laboratories, Inc. under the SER-ALYZER trademark for quantitative determination of cholesterol, uric acid, hemoglobin, triglycerides, and potassium. The test device and methods of the present invention are most useful in end point analysis as opposed to measurement of the rate of change of color for the purpose of determining the relative ultimate concentration of a predetermined component in an assay liquid.

The light reflectance or absorption of the primary chromogen formed by reaction or interaction between the test sample and the reagent strip and the secondary, inert colorant marker are each measured at a light wavelength charactertistic to the particular dyes used. To achieve the full advantage of the present invention, the reflectance of the primary chromogen and the secondary, inert colorant marker are each measured at a light absorption wavelength peak and the primary chromogen and the secondary colorant marker should have light absorption wavelength peaks separated by at least 80 nm.

The apparent concentration of the secondary inert colorant marker is calculated from the reflectance obtained at the absorption maximum and, together with the known concentration of the inert colorant marker, this apparent concentration is used to provide a correction factor for the concentration of the analyte obtained from measuring the reflectance of the primary chromogen at the absorption maximum. This correction factor allows the calculated concentration of the analyte to be corrected for variations in reagent strip characteristics such as thickness and scattering coefficient as well as instrumental variability. Quite surprisingly, the test device and method of the present invention provides about a two-fold improvement in accuracy of concentration measurements. For example, in a cholesterol reagent strip without a secondary, inert colorant marker, the coefficient of variation in replication is about 4% whereas by adding the secondary, inert colorant marker, the coefficient of variation in replication is reduced to less than 2%.

The secondary inert colorant marker is a dye that is inert to the reactant composition contained in the carrier or reagent strip and inert to the sample to be analyzed. The inert dye can be homogeneously mixed into the test sample at a known concentration or impregnated into the reagent strip together with the reactant composition.

In accordance with the present invention, it has been shown that by including a secondary, inert colorant material, together with a primary chromogen or indicator responsive to the concentration of a predetermined component in a sample, the reflectance or absorption measurements made on the secondary, inert colorant material, present in a known concentration, provides an inaccuracy correlation for the reflectance or absorption measurement made on the primary chromogen material regardless of the measurement wavelengths of the inert colorant materials and the chromogen and regardless of the concentration of the predetermined sample component. These results are most unexpected since it might be theorized that inaccuracies in reflectance measurement of one dye might be correlatable to inaccuracies of a measured test component reflectance only if the two dyes have exactly the same reflectance, and only at a particular concentration of analytes. It has been shown, however, that the inaccuracy correlation obtained from the reflectance of a secondary, inert colorant material for correction of the reflectance measurement obtained from the analyte, after substantially complete reaction with the reagent composition of the test device holds true over a wide range of measurement wavelengths (about 300 to about 1000 nm); over a myriad of combinations of inert colorant materials and secondary chromogens (in a reflectance range of about 5 to about 70 percent); and over a wide range of analyte concentrations.

For the secondary, inert colorant marker measurement to provide a useful correction for the concentration of the analyte, the correlation must also hold true in concentration units as well as in reflectance measurements. To verify this, the reflectances were converted to K/S values using the infinite thickness Kubelka-Munk equation:

$$\frac{K}{S} = \frac{(1-R)^2}{2R}$$

and K is the absorption coefficient, S is the scattering coefficient, and R is the reflectance of a sample which is thick enough (infinitely thick) so that its reflectance does not depend on the reflectance of the reagent strip backing or pad support material.

Reagent strips used for the quantitative analysis of glucose in serum or whole blood are well known. The reagent strip includes a reactant system comprising an enzyme, such as glucose oxidase, capable of catalyzing the oxidation reaction of glucose to gluconic acid and hydrogen peroxide; an indicator or oxidizable dye (primary chromogen), such as o-tolidine; and a substance having peroxidative activity capable of catalyzing the oxidation of the indicator. The dye or indicator turns a visually different shade of color depending upon the extent of oxidation -dependent upon the concentration of glucose in the blood sample.

The reactions occurring in the reaction system are represented as follows:

Extant reagent strips generally include a matrix material such as a bibulous, e.g., cellulosic, material impregnated with the reactant composition capable of reacting with glucose as described above, and a matrix overcoating material capable of filtering out blood cells to prevent the blood cells from staining the matrix material.

The color change due to oxidation of the indicator is detected in a reflectance spectrophotometer to determine the concentration of glucose in the test sample (e.g., whole blood).

In addition to whole blood and urine, there are other body fluids from which glucose can be measured. Published data indicate that sweat is an ultrafiltrate of blood with a low, variable glucose concentration. The literature indicates that glucose concentration in the interstitial extracellular space and intramuscular or subcutaneous locations is lower than blood glucose, but this is believed to be a good measure of the blood glucose. Thus, glucose reaches the underside of the skin in potentially useful amounts.

The present invention contemplates in its broader aspects the measurement of any test sample component capable of interaction with a reagent composition to produce a primary chromophore or compound capable of undergoing a color change. The compounds formed during the reaction, involving e.g. glucose, can in turn react with other substances which themselves undergo no or only a slight color change but which react with a colorforming substance to produce a color. More than one substance can mediate between the compounds formed during the reaction and the color-forming substance. Enzymes are biological catalysts and many of them have an unusual specificity for catalyzing a particular reaction with a single, specific and predetermined chemical substance. The glucose, cholesterol and uric acid enzymes, for example, are those which will catalyze a reaction of glucose, cholesterol and uric acid, respectively, when contained in the liquid being tested, thereby producing a predetermined reaction product. The primary chromogen or indicating substance is one capable of forming a color or changing color in the presence of a reaction product or a mediating substance. Any amount of the enzymes and color forming or color changing components sufficient to cause a degree of reactance or a reaction product sufficient to produce a detectable change in the reaction composition can be incorporated in the reactant system of the absorbant or adsorbant material of the test device or reagent strip. Suitable amounts of a glucose, cholesterol, or uric acid enzyme, e.g., glucose oxidase, cholesterol oxidase, or uricase and a substance having peroxidative activity, e.g., horseradish peroxidase, are, for example, 1,000 to 100,000 units into about 20 grams of absorbent matrix material. Suitable amounts of color forming or color changing agents are, for example, .01% to 30% by weight of the total weight of matrix material and reagent composition, on the dry basis, preferably 1 to 10% by weight.

A primary color-forming substance is incorporated into the reactant system (either into the reagent strip or into the test liquid) which will interact with the reagent composition or the test liquid to produce a colored material or a material of a different color from that of the original substance. The color-forming substance may undergo color change not as a result of direct action of a reagent composition compound but can be mediated through another compound which is acted upon by a reaction product but which does not itself become highly colored.

For the quantitative analysis of glucose, the preferred glucose indicator of the reagent composition of the test device of the present invention comprises glucose oxidase and peroxidase or a peroxidase-like substance having peroxidative activity, and a primary chromogen compound capable of forming color or changing color in the presence of hydrogen peroxide. When this reactant system contained in the matrix of the test device of the present invention comes into contact with glucose or a material containing glucose, such as the blood of a diabetic, the peroxidase catalyzes the reaction between hydrogen peroxide and the primary color changing compound to produce the oxidized form of the compound. The primary color changing compound can be any compound capable of producing a color or changing color upon being acted upon by hydrogen peroxide in the presence of the substance having peroxidative activity. More than one substance having peroxidative activity may be present in the reactant system. For example, sodium iodide can be present with tetramethyl benzidine or gum guaiac.

Color-forming substances of peroxidase and peroxidase-like substances which produce a color formation in the presence of hydrogen peroxide and a substance having peroxidative activity for quantitative measurement of glucose, cholesterol and uric acid include the following substances:

(1) Monoamines, such as aniline and its derivatives, ortho-toluidine, para-toluidine, and the like.

(2) Diamines, such as ortho-phenylenediamine, N,N'-dimethyl-para-phenylenediamine, N,N'-diethyl phenylenediamine, benzidine and its derivatives, such as tetramethyl benzidine (which produces a blue or brown color), dianisidine (turns green or brown), and the like;

(3) Phenols, such as phenol per se (producing a yellow color), thymol, ortho-, meta and para-cresols (producing a green-yellow color, a pink color and a milky suspension, respectively, alpha-naphthol (producing a magenta color), betanaphthol (producing a white precipitate), and the like.

(4) Polyphenols, such as catechol, guaiacol (which forms an orange color), orcinol, pyrogallol (producing a reddish or yellow color), p,p-dihydroxydiphenyl and phloroglucinol;

(5) Aromatic acids, such as salicylic, pyrocatechuic and gallic acids;

(6) Leuco dyes, such as leucomalachite green (to produce malachite green) and leucophenolphthalein (desirably employed in an alkaline medium);

(7) Colored dyes, such as 2,6-dichlorophenolindophenol.

(8) Various biological substances, such as epinephrine, the flavones, tyrosine, dihydroxyphenylalanine (producing an orange-reddish color) and tryptophane; and

(9) Other substances, such as gum guaiac, guaiaconic acid, nadi reagent (producing a bluish color), potassium, sodium, and other water soluble iodides; and bilirubin (producing a greenish color).

Typical substances having peroxidative activity include the plant peroxidases, such as horseradish peroxidase or potato peroxidase iodide and molybdate salts such as potassium iodide and sodium molybdate; small measured portions of whole blood, red blood cells alone, lyophylized blood; urohemin and other porphyrin substances having peroxidative activity and other compounds or combinations of compounds, such as disclosed in U.S. Pat. Nos. 3,298,789 and 2,981,606, hereby incorporated by reference.

The test device or reagent strip and methods of the present invention are particularly useful with a reactive system containing a compound capable of catalyzing the reaction between glucose or cholesterol or uric acid and oxygen, such as glucose oxidase where the resulting concentration of $H_2O_2$ formed in the following exemplary catalyzed reaction:

interacts with another reactive system component to produce a visually detectable color change in the carrier matrix. The reflectance of the primary chromogen is detected in a suitable spectrophotometer. In accordance with the present invention, a secondary inert dye included in the reagent system allows correction of the reflectance measurement made on the primary chromogen for substantially improved concentration accuracy. Any other reagent strips used for quantitative measurement of a test sample component also can be improved by incorporating a secondary, inert chromogen dye in a known concentration either into the reagent strip or into the test sample in accordance with the principles of the present invention. Reagent strips now manufactured by the Ames Division of Miles Laboratories, Inc. for the quantitative measurement of cholesterol in serum, similar to the measurement of glucose, rely upon the oxidation of cholesterol in the presence of an enzyme to produce cholestenone and hydrogen peroxide. The hydrogen peroxide formed in the reaction is measured by the oxidation coupling of 3-methyl-1-benzothiazolinone hydrazone (MBTH) and primaquine diphosphate in the presence of peroxidase to form a colored complex. The light reflectance of the colored complex is detected by measuring the reflectance at 600 nm.:

It has been found that the accuracy of the above-described quantitative cholesterol test can be increased about two-fold by including an inert secondary chromogen marker, in a known concentration, into the reagent strip or into the test sample. In accordance with the present invention, a typical reagent composition for cholesterol analysis includes: 1.2% w/w peroxidase—100 IU/mg (horseradish); 2.7% w/w cholesterol oxidase-9.2 units/mg (microbial); 1.0% w/w cholesterol ester hydrolase—15.4 units/mg (microbial); 2.0% w/w 3-methyl-2-benzothiazolinone hydrazone, 15.3% w/w primaquine diphosphate; 9.4% w/w buffer, 0.02% w/w indocyanine green; and the remainder nonreactive ingredients.

Reagent strips now manufactured for quantitative analysis of uric acid in serum are based on the reaction in which hydrogen peroxide, generated by the uricase reaction is measured by oxidative coupling of 3-methyl-2-benzothiazolinone hydrazone (MBTH) and primaquine diphosphate in the presence of peroxidase. The method involves two separate reactions. In the first reaction, uric acid, oxygen and water in the presence of uricase produce allantoin, carbon dioxide and hydrogen peroxide.

The hydrogen peroxide generated in the first reaction then combines with MBTH and primaquine diphosphate in the presence of peroxidase to form a colored complex:

After an incubation period, the concentration of serum uric acid is determined by measuring the change in reflectance at 560 nm. Similarly, the accuracy of the above-described quantitative uric acid test can be increased about two-fold by including an inert, secondary chromogen marker, in a known concentration, into the reagent strip or into the test sample. A typical reagent strip for uric acid analysis contains 13.4% w/w primaquine diphosphate; 8.3% w/w methyl benzothiazolinone hydrazone; 5.5% w/w buffer; 29.1% w/w uricase (hog liver); 2.6% w/w Peroxidase (horseradish); 0.08% w/w indocyanine green; and the remainder being nonreactive ingredients. The secondary, inert dye is measured at 800 nm to obtain a correction factor for the reflectance of the primary chromogen at 560 nm.

In accordance with the present invention, the secondary, inert chromogen, e.g., indocyanine green, is included in the reagent strip, or in the test sample (serum) in an amount of about $2 \times 10^{-4}$ to $2 \times 10^{-1}$ weight percent for unexpectedly increased accuracy in concentration measurements. Other suitable secondary, inert colorant markers, dyes, or colorant materials for any of the reagent strips disclosed herein, which can be used so long as they are inert to the reagent composition and the test sample, include 3,3'-diethylthiatricarbocyanine iodide; 1,1'3,3,3'3'-hexamethyl-4,4',5,5'-dibenzo-2,2'-indotricarbocyanine perchlorate; 1,1'-diethyl-4,4'-carbocyanine iodide; 5,5',-dichloro-11-diphenylamino-3,3'-diethyl-10,12-ethylenethiatricarbocyanine perchlorate; anhydro-1,1-dimethyl-2-(7-(1,1-dimethyl-3-(4-sulfobutyl)-2-(1H)-benzeindolinylidene)-1,3,5-heptatrienyl)3-(4-sulfobutyl) -1H-benz(e)-indolium hydroxide sodium salt; (anhydro-11-(4-ethoxycarbonylpiperazin-1-yl) 10,12-ethylene-3,3,3',3'-tetramethyl-1,1'-bis (3-sulfopropyl)-4,4',5,5'-dibenzoindotricarbocyanine hydroxide triethylamine salt; and thionin. All of these dyes have been shown to provide effective correlations in reflectance readings for correction of the detected reflectance measurements of a primary chromogen material formed proportionately to a concentration of a predetermined test sample component.

Reagent strips now manufactured for the quantitative analysis of hemoglobin in whole blood are based on the quantitation of hemoglobin in the form of methemoglobin. Hemoglobin is freed from erythrocytes by lysis of the cell membrane. The divalent iron in hemoglobin is then oxidized to the trivalent state by potassium ferricyanide to form methemoglobin. The extent of color at 535 nm (primary chromogen) is proportional to the concentration of methemoglobin (endogenous and newly converted) in the reacted specimen.

After an incubation and test period of 45 to 180 seconds, the concentration of hemoglobin in the blood specimen is determined by measuring the reflectance at 535 nm (characteristic of methemoglobin).

In accordance with the present invention, a typical reagent composition for the abovedescribed reaction contains 49% w/w potassium ferricyanide; 39% w/w phosphate buffer; .05% w/w 1,1'-diethyl-4,4'-carbocyanine iodide as a secondary dye, and the remainder nonreactive components. In accordance with the present invention reflectance measurements are made at 535 nm (primary) and at 710 nm (secondary chromogen) for correction of the 535 nm reading.

Reagent strips used for the quantitative analysis of triglycerides from serum or plasma are based on the enzymatic and colorimetric determination of glycerol released from triglycerides. The sequential reactions involved in this process are:

Glycerol, endogenous and that produced by the enzymatic hydrolysis of triglycerides, is phosphorylated by adenosine triphosphate (ATP) to produce glycerol-3-phosphate and ADP in the reaction catalyzed by glycerol kinase (GK). Glycerol-3-phosphate dehydrogenase (G-3-PDH) catalyzes the oxidation of the glycerol-3-phosphate in the presence of nicotinamide adenine dinucleotide (NAD) to produce NADH. The NADH is used to reduce the formazan dye (int) in the reaction catalyzed by diaphorase. A reflectance photometer determines the concentration of sample triglycerides by measuring the change in reflectance of primary and secondary chromogens. In accordance with the present invention, the secondary chromogen is included in the triglyceride reagent strip, or in the test sample (serum) in an amount of about $2 \times 10^{-4}$ to $2 \times 10^{-1}$ weight percent for unexpectedly increased accuracy in concentration measurements.

A typical reagent composition for the abovedescribed triglyceride quantitation includes 1.2% w/w lipase (microbial - 3600 IU/mg; 0.5% w/w glycerol kinase (microbial - 60 IU/mg; 1.1% w/w glycerol-3-phosphate dehydrogenase (rabbit)-110 IU/mg; 1.4 w/w diaphorase (microbial)-35 IU/mg; 7.3% w/w NAD; 3.0% w/w ATP, disodium salt; 1.6% w/w magnesium sulfate, heptahydrate; 5.0% w/w INT; .025% w/w 1,1-dimethyl-2-(7-(1,1-dimethyl-3-(4-sulfobutyl)-2-(1H)-benze(e)indolinylidene)-1,3,5-heptatrienyl)3-(4-sulfobutyl)-1H-benz(e)indolium hydroxide sodium salt); 71% w/w Gelatin; and the remainder non-reactive ingredients. The reagent composition is cast as a film onto a support strip, e.g., a layer of polyethylene terephthalate, and desired reflectance measurements are made at 580 nm (primary chromogen) and 790 nm (secondary, inert chromogen).

Reagent strips used for the quantitative analysis of potassium in serum or plasma are based on a colorimetric, ionophore-mediated, cation-proton exchange reaction between an aqueous and an organic phase. The reagent area consists of a paper matrix containing the organic phase and the ingredients of the aqueous phase. When a sample is applied, the aqueous buffer is dissolved and the aqueous phase is reconstituted. The $K^+$-selective ionophore, 2,3-(naphtho)-15-crown-5, in the organic phase mediates transfer of potassium ions from the aqueous phase to the organic phase. Charge neutrality in the organic phase is maintained by the simultaneous loss of a proton from the indicator dye, 7-decyl-MeDPIN, in the same phase. Deprotonation of the dye results in the appearance of an absorption peak at 640 nm. The reaction scheme is:

The extent of color development by the reaction is proportional to the level of potassium in the sample and is monitored by reflectance spectroscopy at 640 nm (primary chromogen).

In accordance with the present invention, the reagent composition for potassium analysis is, for example, 2.4% w/w 7-(n-Decyl)-2-methyl-4-(3',5'-dichlorphen-4'-one)-indonaphthol; 6.9% w/w 2,3-naptho-15-crown-5; 83.0% w/w buffer; 0.016% w/w 5,5'-dichloro-11-diphenylamino-3,3'-diethyl-10,12-ethylene-thiatricarbocyanine perchlorate and the remainder nonreactive ingredients. The reagent composition is impregnated into a filter paper and reflectance measurements are made at 640 nm (primary chromogen) and 800 nm (secondary chromogen).

In accordance with the present invention, the secondary chromogen is included in the potassium reagent strip, or in the test sample (serum) in an amount of about $2 \times 10^{-4}$ to $2 \times 10^{-1}$ weight percent for unexpectedly increased accuracy in concentration measurements.

In accordance with the present invention, it has been found that highly significant correlations exist between (1) the calculable measurement inaccuracy of a secondary, inert chromogen dye marker when incorporated into a reagent strip or test sample, and (2) a measured reflectance of a primary chromogen dye colorimetrically responsive to an interaction between the reagent composition and a predetermined component of a test sample. The secondary, inert chromogen marker is capable of correlating primary chromogen reflectance measurements to achieve approximately a two-fold increase in measurement accuracy. The secondary, inert chromogen marker corrects for variations in reagent pad scattering coefficient, pad thickness, pad volume, reflectance of reagent strip backing or support material, height variability of the reagent pad, position variability of the reagent pad and drift within the specrophotometer. Quite surprisingly, the measured reflectance of the primary chromogen is highly correlatable to the inaccuracy in reflectance measurement of the secondary, inert marker chromogen, regardless of concentrations and wavelength of the secondary chromogen, so long as the reflectance absorption wavelength peak for the primary and secondary chromogen dyes are separated by at least 80 nm.

As examples of corrections of a primary chromogen reflectance measurement based on an expected and observed reflectance measurement of a secondary, inert dye, the following calculations shown in Examples 1–3 with and without the correction, are based upon the uric acid reagent formulation set forth at the bottom of page 19 of the specification:

CALCULATION FORMULA WITHOUT CORRECTION $$X = L + \frac{(H-L)(K_{X1} - K_{L1})}{K_{H1} - K_{L1}}$$

CALCULATION FORMULA WITH CORRECTION $$X = \left[ L + \frac{(H-L)(K_{X1} - K_{L1})}{K_{H1} - K_{L1}} \right] \frac{(K_{L2} + K_{H2})}{2K_{X2}}$$

wherein:
L = concentration of low calibrator
H = concentration of high calibrator
$K_{X1}$ = K/S for sample at primary chromogen wavelength
$K_{X2}$ = K/S for sample at secondary chromogen wavelength
$K_{L1}$ = K/S for low calibrator at primary chromogen wavelength
$K_{L2}$ = K/S for low calibrator at secondary chromogen wavelength
$K_{H1}$ = K/S for high calibrator at primary chromogen wavelength
$K_{H2}$ = K/S for high calibrator at secondary chromogen wavelength; and
X = concentration of sample
and the data for the calibrators is
L = 1.9 mg/dl
H = 7.2 mg/dl
$K_{L1}$ = 0.6644
$K_{L2}$ = 1.124
$K_{H1}$ = 1.717
$K_{H2}$ = 1.102

Data for samples
Example 1:
    Assayed at 1.9 mg/dl
    $K_{X1}$ = 0.7168
    $K_{X2}$ = 1.312
Calculated value without correction =
    2.16 mg/dl. Error = −13.9%
Calculated value with correction =
    1.83 mg/dl. Error = −3.7%
Sample Two
    Assayed at 4.5 mg/dl.
    $K_{X1}$ = 1.103
    $K_{X2}$ = 0.998
Calculated value without correction =
    4.108 mg/dl. Error = −8.7%
Calculated value with correction =
    4.58 mg/dl. Error = +1.8%
Sample Three
    Assayed at 7.2 mg/dl.
    $K_{X1}$ = 1.400
    $K_{X2}$ = 0.9199
Calculated value without correction =
    5.60 mg/dl Error = −22.2%
Calculated value with correction =
    6.78 mg/dl Error = −5.8%

Figure 1:
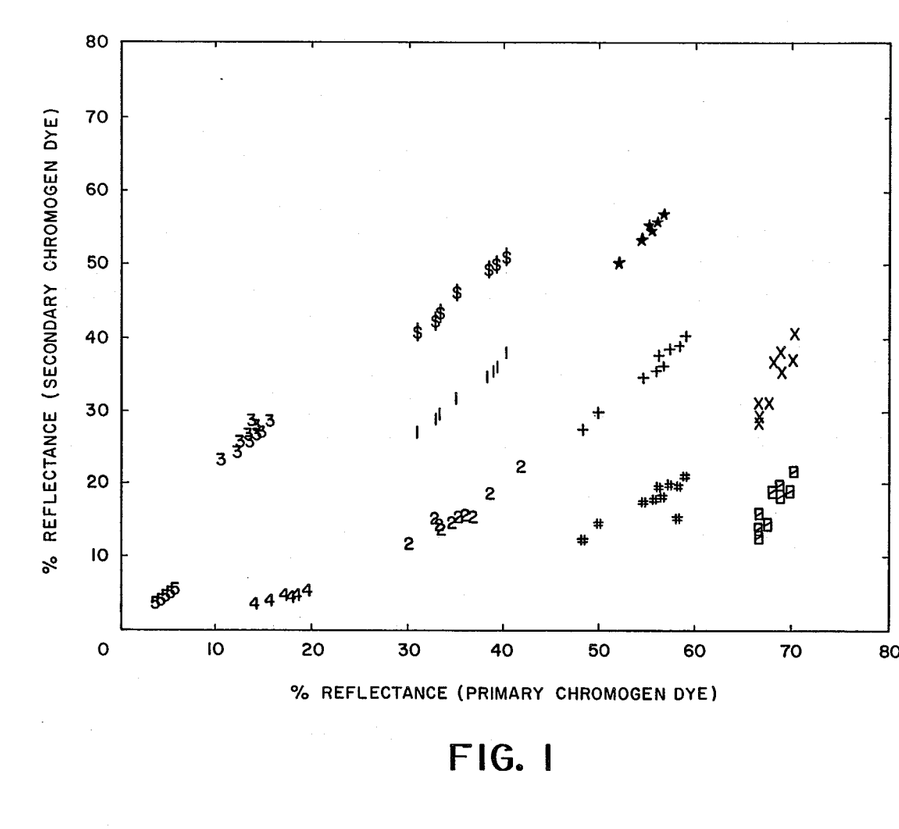
FIG. 1 is a graph comparing reflectance of primary and secondary chromogen compounds measured at various wavelengths and concentrations showing that an increase in reflectance measured for the secondary dye relates to an increased reflectance measurement for the primary chromogen.

As shown in FIG. 1, data obtained with various mixtures of amaranth as the primary chromogen and various concentrations of 3,3'-diethylthiatricarbocyanine iodide as an inert, secondary chromogen dye, measured at different wavelength and concentration combinations, provided a wide range of reflectances for both the primary and secondary dyes. Aqueous mixtures of the primary and secondary dyes at various concentrations were prepared. Seven microliters of the mixture were pipetted onto each pad (0.5 by 1 cm or 0.2 by 0.4 inch) of filter paper type 54 (Whatman, Inc. of Clifton, N.J.) and reflectance measurements made at various wavelengths to determine if there is a correlation between reflectance measurements of the primary and secondary chromogen dyes. Table I shows the wavelengths measured and concentrations corresponding to the symbols in FIG. 1.

TABLE I

Concentrations and wavelengths for FIG. 1

| Symbol | Primary Chromogen (Amaranth) Molar Conc. | nm | Secondary Chromogen (3,3'diethylthia-tricarbocyanine iodide) Molar Conc. | nm |
|---|---|---|---|---|
| * | $1 \times 10^{-4}$ | 420 | $3 \times 10^{-5}$ | 600 |
| $ | $3 \times 10^{-4}$ | 520 | $1 \times 10^{-4}$ | 600 |
| X | $3 \times 10^{-5}$ | 520 | $3 \times 10^{-4}$ | 600 |
| 0 | $3 \times 10^{-5}$ | 520 | $3 \times 10^{-4}$ | 680 |
| + | $1 \times 10^{-4}$ | 420 | $3 \times 10^{-4}$ | 600 |
| # | $1 \times 10^{-4}$ | 420 | $3 \times 10^{-4}$ | 680 |
| 1 | $3 \times 10^{-4}$ | 520 | $1 \times 10^{-4}$ | 700 |
| 2 | $1 \times 10^{-3}$ | 420 | $3 \times 10^{-4}$ | 700 |
| 3 | $1 \times 10^{-3}$ | 520 | $3 \times 10^{-4}$ | 600 |
| 4 | $3 \times 10^{-3}$ | 500 | $1 \times 10^{-3}$ | 700 |
| 5 | $3 \times 10^{-3}$ | 420 | $1 \times 10^{-3}$ | 700 |

As shown in FIG. 1, an increase in reflectance measured for the secondary chromogen dye, at any given wavelength measured and any concentration, results in a similar increase in the measured reflectance of the primary chromogen dye. Therefore, the use of two wavelength measurements (one for the primary chromogen dye and one for the secondary chromogen dye) showed correlations useful for compensations of the inaccuracies in the measured reflectance of the primary chromogen dye due to variations in reagent strips and the spectrophotometer response. The data of FIG. 1 shows that the reflectances for the primary and secondary chromogen dyes need not be identical for useful correlations.

Figure 2:
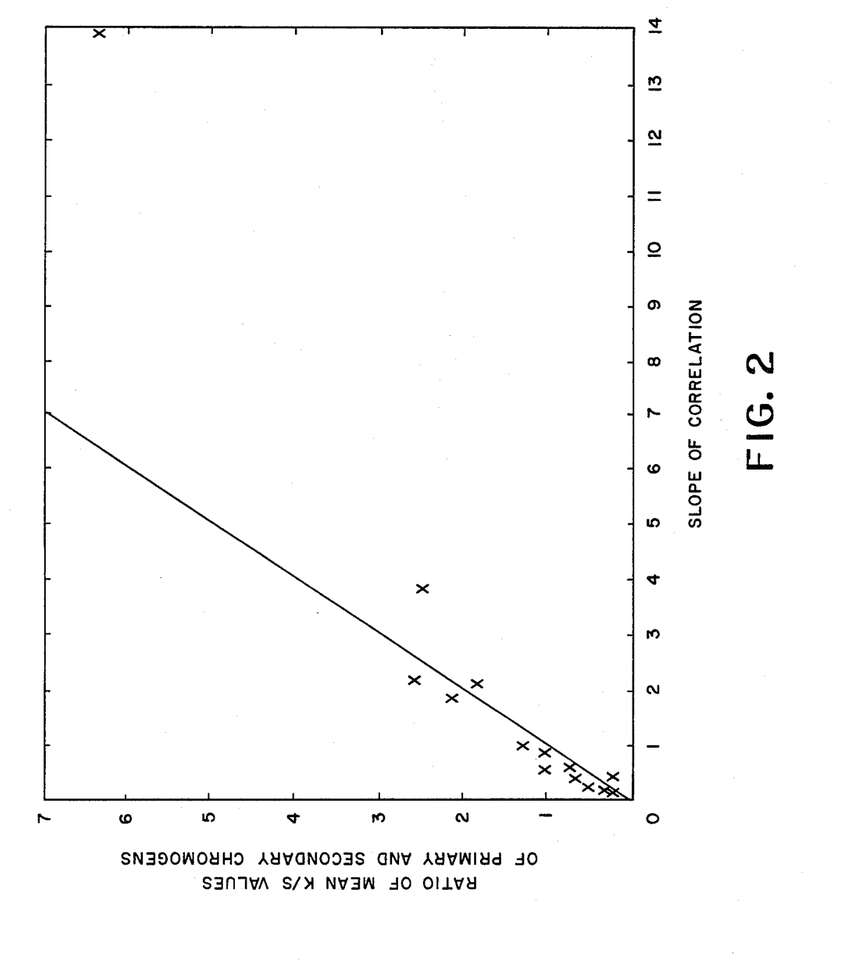
FIG. 2 is a graph showing the relationship between K/S of the primary chromogen and the secondary, inert chromogen versus the slope of the correlation of the K/S of the primary chromogen to the K/S of the secondary chromogen.

For the secondary chromogen marker measurement to provide a useful correction for the concentration of the analyte, the correlation must hold in concentration units. To verify this, as shown in FIG. 2, reflectance measurements similar to those of FIG. 1 were converted to K/S values using the infinite thickness Kubelka-Munk equation. The correlations observed were very similar to those observed in reflectance measurements. If the percent variations in K/S are the same for the primary and secondary chromogens, a plot of the ratio of the K/S values for the primary and secondary chromogens versus the slope of the correlation between the K/S values for the primary and secondary chromogen dyes should have a slope of unity. This relationship, shown in FIG. 2, is quite surprising in the art and enables correction of primary chromogen concentration measurements. The outlier measurement in the upper right hand corner of FIG. 2 occurred at a very high value of K/S where the reflectance rrom the pad surface is significant and influences the value of K/S.

The residual error from the correlations of FIG. 1 corresponds to a coefficient of variation in concentration units in the range of 1.5 to 2%. This is much better than can be obtained in single wavelength determinations.

QUANTITATIVE CHOLESTEROL DETERMINATION

A paper reagent strip was impregnated with 1.2% w/w peroxidase-103 IU/mg (horseradish); 2.7% w/w cholesterol oxidase-9.2 units/mg (microbial); 1.0% w/w cholesterol ester hydrolase-15.4 units/mg (microbial); 2.0% w/w 3-methyl-2-benzothiazolinone hydrazone; 15.3% w/w primaquine diphosphate; 9.4% w/w buffer and 0.02% indocyanine green dye with the remaining components nonreactive solvents and the like, as obtained from the Ames Division of Miles Laboratories, Inc. SERALYZER Cholesterol reagent strips.

Figure 3:
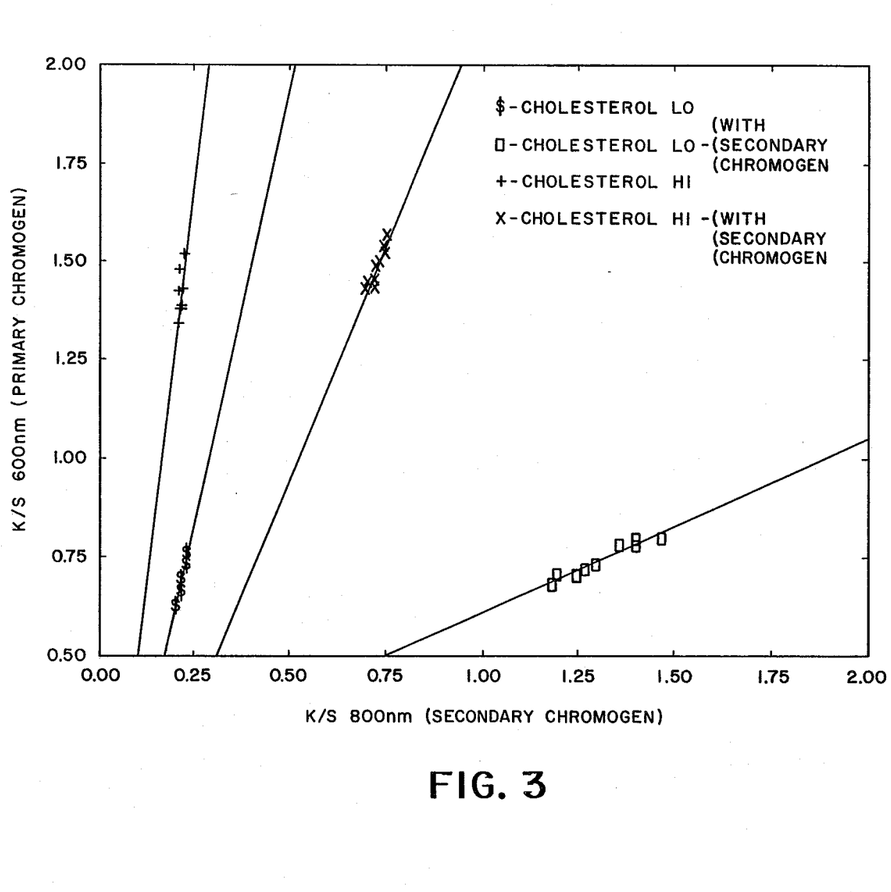
FIG. 3 is a graph showing the relationship between K/S for a cholesterol (primary) chromogen and an indocyanine green secondary chromogen measured at the absorption maximums for each chromogen and at various cholesterol concentrations, with and without the secondary chromogen.

Data obtained with the cholesterol reagent are shown in FIG. 3. Although a correlation is apparent in the absence of the internal standard (as shown in Table II, data at left, it is not good enough to improve performance. With the secondary, inert chromogen marker present in the reagent, as shown by the data at the right of Table II; a surprisingly better correlation is observed and correction of the data permits a two-fold improvement in performance. The coefficients of variation are given in Table II. The inert, secondary chromogen dye theoretically can give a precision in replication of 1.5%. This is much better than is obtainable with the current reagent strips measuring reflectance of a primary chromogen dye only.

TABLE II

| CHOLESTEROL COEFFICIENTS OF VARIATION | | |
|---|---|---|
| CHOLESTEROL | SINGLE WAVELENGTH | DUAL WAVELENGTH |
| Low (0.13 wt. %) | 5.1 | 1.8 |
| High (0.4 wt. %) | 4.5 | 3.1 |
| Low + indocyanine green | 5.7 | 1.5 |
| High + indocyanine green | 3.6 | 1.4 |

QUANTITATIVE URIC ACID DETERMINATION

A paper reagent strip was impregnated with 13.4% w/w primaquine diphosphate; 8.3% w/w methyl benzothiazolinone hydrazone; 5.5% w/w buffer; 29.1% w/w uricase (hog liver); 2.6% w/w peroxidase (horseradish); and 0.08% w/w indocyanine green dye, the remainder of the reagent composition being nonreactive solvents and the like, as obtained from Ames Division of Miles Laboratories, Inc. SERALYZER Uric Acid reagent strips.

Figure 4:
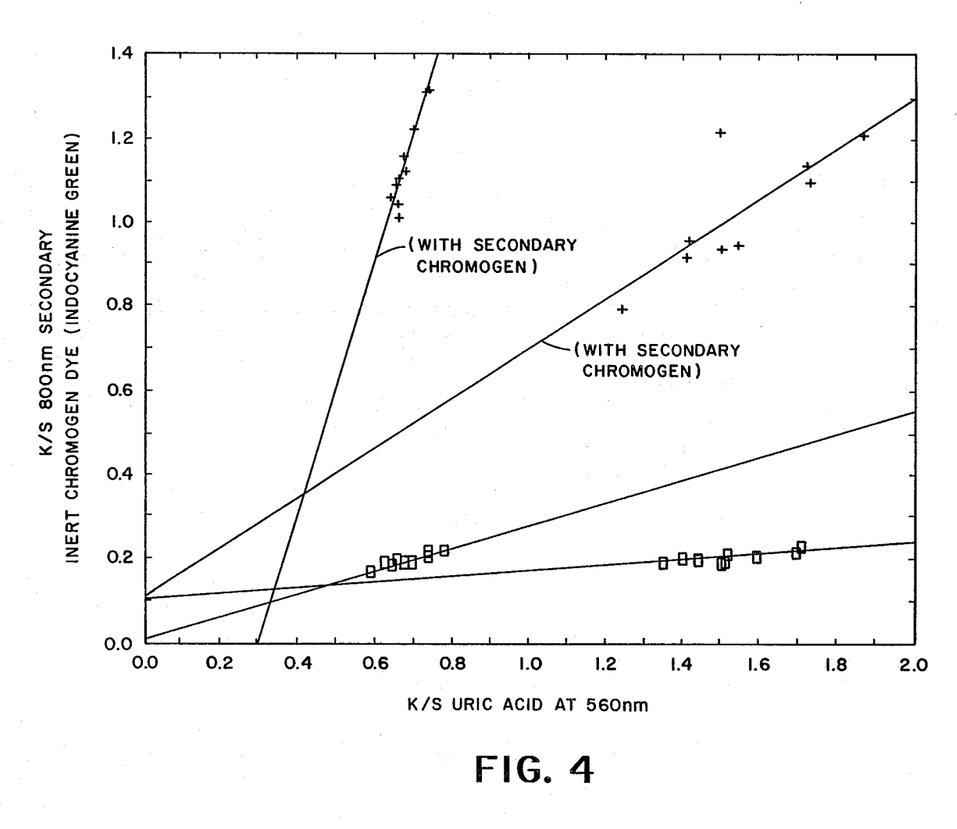
FIG. 4 is a graph showing the relationship between K/S for the uric acid (primary) chromogen and an indocyanine green secondary chromogen measured at the absorption maximums for each chromogen and at various uric acid concentrations, with and without the secondary chromogen.

For uric acid, the behavior was similar to cholesterol. Plots of K/S data are shown in FIG. 4. The coefficients of variation are given in Table III. If the outlier evident in the upper right of the figure were removed, the coefficient of variation for the high uric acid sample with internal standard would drop to 3.5%.

TABLE III

| URIC ACID COEFFICIENTS OF VARIATION | | |
|---|---|---|
| URIC ACID | SINGLE WAVELENGTH | DUAL WAVELENGTH |
| Low (0.0019 wt. %) | 7.6 | 2.6 |
| High (0.0072 wt. %) | 7.7 | 4.5 |
| Low + indocyanine green | 4.9 | 1.9 |
| High + indocyanine green | 12.3 | 7.8 | the reagent systems for BUN (blood urea nitrogen) and creatinine measure the rate of change of the indicator K/S. Attempts to correlate the rate of change of the indicator K/S to the constant K/S of the internal standard did not produce useful relations for these reagents.

QUANTITATIVE HEMOGLOBIN DETERMINATION

A macroporous polyurethane strip was impregnated with a reagent composition comprising 49% w/w potassium ferricyanide; 39% w/w phosphate buffer; and 0.05% w/w/ 1,1'-diethyl-4,4'-carbocyanine iodide with the remainder nonreactive components. The strip then was contacted with a drop of whole blood and reflectance measurements made at 535 nm and 710 nm. The reflectance measurement of the secondary, inert dye at 710 nm enables correction of the reflectance measurement measured at 535 nm permitting an approximate doubling of the accuracy of the calculated hemoglobin concentration in the blood sample.

QUANTITATIVE TRIGLYCERIDES DETERMINATION

A reagent composition containing 1.2% w/w lipase (microbial)-3600 IU/mg; 0.5% w/w glycerol kinase (microbial)-60 IU/mg; 1.1% w/w glycerol-3-phohsphate dehydrogenase (rabbit)-110 IU/mg; 1.4% w/w diaphorase (microbial)-35 IU/mg; 7.3% w/w NAD; 3.0% w/w ATP, disodium salts; 1.6% w/w magnesium sulfate, heptahydrate; 5.0% w/w INT; 0.025% w/w 1,1-dimethyl-2-(7-(1,1-dimethyl-3-(4-sulfobutyl)-2-(1H)-benz(e) indolinylidene)-1,3,5-heptatrienyl)3-(4-sulfobutyl) -1H-benz(e)-indolium hydroxide sodium salt); 71% w/w gelatin and the remainder nonreactive ingredients. The reagent composition is cast as a film and dried. The film was contacted with a drop of serum and reflectance measurements are made at 580 nm and 790 nm. The reflectance measurement of the secondary, inert dye at 790 nm enables correction of the reflectance measurement measured at 50 nm permitting an appreciative doubling of the accuracy of the calculated triglycerides concentration in the serum sample.

QUANTITATIVE POTASSIUM DETERMINATION

A filter paper reagent strip was impregnated with a reagent composition containing 2.4% w/w 7-(n-Decyl)-2-methyl-4-(3',5'-dichlorophen-4'-one)indonaphthol; 6.9% w/w 2,3-naphtho-15-crown-5; 83.0% w/w buffer 0.016% w/w 5,5'-dichloro-11-diphenylamino-3,3'-diethyl-10,12-ethylenethiatricarbocyanine perchlorate; with the remainder nonreactive components. The reagent strip is contacted with a drop of serum and reflectance measurements made at 640 nm and 800 nm. The reflectance measurement of the secondary, inert dye at 800 nm enables correction of the reflectance measurement at 640 nm permitting an approximate doubling of the accuracy of the calculated potassium concentration in the serum sample.

Many modifications and variations of rhe present invention are possible in light of the above teachings. Thus, it is to be understood that, within the scope of the appended claims, the invention may be practiced other than as specifically described.

What is claimed and desired to be secured by Letters Patent is:

1. A test article for detecting a relative concentration of a test compound in a test fluid comprising a liquid-absorbent or liqudi-adsorbent dry reagent carrier having homogeneously incorporated therein a regent composition capable of forming a primary color upon interaction with the test fluid to produce a change in the light reflectance of the carrier, and a secondary, inert colorant marker homogeneously incorporated into the carrier or the test fluid in a predetermined concentration, said colorant marker being inert to the test fluid and to the reagent composition and wherein the secondary, inert colorant marker has a light absorption wavelength peak different from a light absorption wavelength peak of the primary color by at lest 80 nm.

2. The test article of claim 1 wherein the reagent carrier comprises a bibulous material.

3. The test article of claim 1 wherein the secondary, inert colorant marker comprises a dye having a high absorption maximum peak separated by at least 120 nm from a light absorption maximum peak of the primary color formed by contact of the test article with a test sample.

4. A reagent strip for sensing the presence of a chemical compound in an assay liquid, comprising:
   a dry carrier material capable of absorbing or adsorbing a liquid reactant composition for uniform distribution of the reactant compsition therein; and
   a reactant composition uniformly distributed throughout the carrier;
   said reactant composition including a compound capable of interaction with a predetermined component of the assay liquid to form a primary color in the reactant composition to produce a detectable change in the light reflectance of the carrier at a predetermined wavelength; said reactant composition also including a secondary, inert colorant marker material having a light absorption wavelength peak different from the light absorption wavelength peak of the primary color by at least 80 nm.

5. The reagent strip of claim 4 wherein the reagent carrier comprises a liquid-absorbant or liquid-adsorbant bibulous material.

6. The reagent strip of claim 4 wherein inert colorant marker comprises a dye having a high absorption maximum peak separated by at least 120 nm from a light absorption maximum peak of the primary color.

7. In a dry test device for the quantitative measurement of a compound in a test liquid wherein the test device includes a reagent composition capable of interaction with the compound of the test liquid to produce a primary detectable color in the reagent composition after contact of the reagent composition with the test liquid, the improvement comprising a secondary colorant material inert to the test liquid and inert to the reagent composition homogeneously incorporated in the reagent composition or homogeneously incorporated in the test liquid in a known concentration and having a light absorption wavelength peak different form that of the primary formed color by at least 80 nm.

8. The test device of claim 7 wherein the reagent carrier comprises liquid-abosrbant or liquid-adsorbant bibulous material.

9. The test device of claim 7 wherein the secondary, inert colorant material comprises a dye having a high absorption maximum peak separated by at least 120 nm from a light absorption maximum peak of the primary color formed by contact of the test device with the test liquid.

10. A method of measuring the concentration of a predetermined chemical compound in an assay liquid comprising:
   distributing a predetermined quantity of a reagent composition into a liquid-absorbent or liquid-adsorbent reagent carrier, wherein the reagent composition includes a compound capable of interaction with a predetermined componet of the assay liquid to cause a detectable change in the light reflectance of the carrier at a predetermined wavelength by formation of color or a color change in a primary chromogen; said reactant composition also including a secondary, inert colorant marker material having a light absorption wavelength peak different from a light absorption wavelength peak of the primary chromogen by at least 80 nm;
   drying the carrier;
   contacting a surface of the dried carrier with the assay liquid to cause color changes detectable at wavelengths characteristic to both the primary chromogen and the secondary colorant in said carrier;
   detecting the light refelctance of the carrier at a wavelength characteristic of the light reflectance of the primary chromogen, and detecting the light reflectance of the carrier at a wavelength characteristic of the light reflectance of the secondary, inert colorant marker material;
   determining the concentration of said predetermined chemical compound based upon the degree of color change in the primary chromogen; and
   correcting the concentration determination based upon the light reflectance measurement for the secondary chromogen.

11. The method of claim 10 wherein the reflectance measurements of the carrier are made at the absorption maximums for the primary chromogen and the secondary, inert colorant marker materials.

12. The method of claim 10 wherein the assay liquid is a biological fluid.

13. The method of claim 12 wherein the assay liquid is whole blood, serum, or plasma.

14. A method of measuring the concentration of a predetermined chemical compound in an assay liquid comprising:
   distributing a predetermined quantity of a reagent composition into a reagent carrier, wherein the reagent compositon includes a compound capable of interaction with a predetermined component of the assay liquid to cause a detectable change in the light reflectance of the carrier at predetermined determined wavelength by formation of color or a color change in a primary chromogen; said reactant composition also including a secondary, inert colorant marker material having a light absorption wavelength peak differnet from a light absorption wavelength peak of the primary chromogen by at least 80 nm;
   drying the carrier;
   contacting a surface of the dried carrier with the assay liquid to cause color changes detectable at wavelengths characteristic to both the primary chromogen and the secondary colorant in said carrier;
   detecting the light reflectance of the carrier at a wavelength characteristic of the light reflectance of the primary chromogen, and detecting the light reflectance of the carrier at a wavelength characteristic of the light reflectance of the secondary, inert colorant marker material;

determining the concentration X of said predetermined chemical compound by the formula:

$$X = \left[ L + \frac{(H - L)(K_{X1} - K_{L1})}{K_{H1} - K_{L1}} \right] \left[ \frac{K_{L2} + K_{H2}}{2K_{X2}} \right]$$

wherien the term $$L + \frac{(H - L)(K_{X1} - K_{L1})}{K_{H1} - K_{L1}}$$

is representative of the degree of color change in the primary chromogen and the term $$\frac{K_{L2} + K_{H2}}{2K_{X2}}$$

is the correction factor upon the light reflectance measurement for the secondary marker material, wherein X=analyte concentration of test sample;

L=analyte concentration of a low concentration calibrator solution;

H=analyte concentration of a high concentration calibrator solution;

$K_{X1}$=K/S for sample at primary chromogen wavelength;

$K_{L1}$=K/S for low calibrator at primary chromogen wavelength;

$K_{H1}$=K/S for high calibrator at primary chromogen wavelength;

$K_{L2}$=K/S for low calibrator at secondary chromogen wavelength;

$K_{H2}$=K/S for high calibrator at secondary chromogen wavelength;

$K_{X2}$=K/S for sample at secondary chromogen wavelength; and $$K/S = \frac{(1 - R)^2}{2R}.$$

wherein K is the absorption coefficient, S is the scattering coefficient, and R is the reflectance; and correcting the concentration determination made for the predetermined chemical compound in accordance with said formula based upon the reflectance measurement for the secondary chromogen.

* * * * *